US005362748A

United States Patent [19]
Schwen et al.

[11] Patent Number: 5,362,748
[45] Date of Patent: Nov. 8, 1994

[54] METHODS OF USING DIETHYLDITHIOCARBAMIC ACID FOR THE PREVENTION OF HAIR GROWTH

[75] Inventors: Richard J. Schwen, Cincinnati; Donald L. Bissett, Hamilton, both of Ohio

[73] Assignee: The Procter & Gamble Company, Cincinnati, Ohio

[21] Appl. No.: 121,823

[22] Filed: Sep. 15, 1993

[51] Int. Cl.$^5$ .............................. A61K 31/27
[52] U.S. Cl. .................................... 514/476
[58] Field of Search ........................... 514/476

[56] References Cited

U.S. PATENT DOCUMENTS 4,814,351  3/1989  Mathews et al. ............. 514/566

FOREIGN PATENT DOCUMENTS

WO92/03140  3/1992  WIPO .

OTHER PUBLICATIONS

Blumenkrantz N. and L. Blomstedt, "Chelators Depigmant and Increase Elasticity of Mink Skin", *Acta. Agric. Scand.*, vol. 37, pp. 375–395, (1987).

Milas, L., N. Hunter, H. Ito, and L. J. Peters, "In Vivo Radioprotective Activities of Diethyldithiocarbamate (DDC)", *Int. J. Radiation Oncology Biol. Phys.*, vol. 10, pp. 2335–2343, (1984).

Schoental, R., "Irreversible Depigmentation of Hair by N-Methyl-N-Nitrosourethane", *Experientia*, vol. 27, pp. 552–553, (1987).

Sunderman, F. W., "Use of Sodium Diethyldithiocarbamate in the Treatment of Nickel Carbonyl Poisoning", *Annals of Clinical and Laboratory Science*, vol. 20, No. 1, pp. 14–21, (1990).

*Primary Examiner*—Alan Seigel
*Attorney, Agent, or Firm*—Soma G. Simon; David L. Suter; Milton B. Graff, IV

[57] ABSTRACT

The subject invention relates to methods for regulating hair growth in mammalian skin comprising topical application of diethyldithiocarbamic acid ("DEDCA") or a pharmaceutically-acceptable salt thereof. The subject invention further involves topical compositions comprising DEDCA.

8 Claims, No Drawings

METHODS OF USING DIETHYLDITHIOCARBAMIC ACID FOR THE PREVENTION OF HAIR GROWTH

TECHNICAL FIELD

The subject invention relates to the field of regulation of hair growth in mammalian skin. Specifically, the subject invention relates to methods for the suppression and/or retardation of hair growth in humans.

BACKGROUND

The removal of hair from the human body has received considerable attention, both for medical and for cosmetic reasons. Various methods exist to remove unwanted hair. Conventional methods focus on mechanical removal and chemical depilation, whereby unwanted hair is removed once it has already appeared above the surface of the skin. Other methods involve the prevention, suppression or retardation of hair growth, by an alteration in the rate and character of hair growth.

Mechanical methods employed for depilation include tweezing, plucking, electrolysis, shaving and X-ray techniques. Tweezing and plucking are of limited utility because their use is confined to a localized area. Electrolysis and X-ray techniques are painful and require the use of expensive equipment, while shaving frequently stimulates rapid hair growth and leads to skin irritation.

Chemical depilatory compositions are effective in removing unwanted hair from larger areas on the skin. These compositions typically cleave disulfide bonds in hair keratin, causing the hair fiber to disintegrate. However, most chemical depilatory compositions are strongly alkaline, causing dermal irritation, particularly on sensitive facial skin.

At present, compositions generally called "waxes" are also used for depilation. These are applied to the skin in a molten state. On cooling and hardening, the wax enmeshes the hair it contacts. The wax is thin stripped from the skin, pulling out the enmeshed hair by its roots. Even though waxing is longer-lasting than other chemical methods, it is disfavored because of the tendency to cause irritation, swelling or possible burning.

Of the methods employed to alter the rate and character of hair growth, most involve the application of anti-androgens to control dermatological conditions associated with androgen-dependent disorders, such as female hirsutism. However, these methods have undesirable side effects such as systemic anti-androgen effects, teratogenecity and pituitary dysfunction and are, consequently, of limited use.

For the foregoing reasons, there is a need to develop a method which is efficacious, easily administered, non-irritating, long-lasting, and can regulate the growth of unwanted hair without allowing rapid return growth.

It is an object of the subject invention to provide topical compositions for retarding or preventing the growth of hair in mammalian skin.

It is a further object of the subject invention to provide such compositions which are gentler and less irritating to the skin than existing compositions.

It is also an object of the subject invention to provide methods for retarding or preventing the growth of hair in mammalian skin.

SUMMARY OF THE INVENTION

The subject invention involves topical compositions for regulating hair growth in a mammal susceptible to or suffering from hirsutism or unwanted hair, comprising diethyldithiocarbamic acid ("DEDCA") in a pharmaceutically-acceptable carrier. The subject invention further involves methods comprising topically applying to the skin of the mammal a safe and effective amount of DEDCA.

DETAILED DESCRIPTION OF THE INVENTION

It has been found that compositions containing DEDCA, a chelator, exhibit the ability to regulate hair growth in mammalian skin, without undesirable side effects, such as skin irritation, commonly associated with known compositions for regulating hair growth. While the subject invention is not limited to any particular mode of action, it is believed that DEDCA may regulate hair growth by tying up essential metal ions necessary for hair growth.

As used herein, "diethyldithiocarbamic acid" and "DEDCA" mean the compound having the structure:

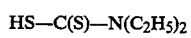

$$HS-C(S)-N(C_2H_5)_2$$

As used herein, "topical application" means directly laying on or spreading on the skin of a mammal.

As used herein, "safe and effective amount" means an amount of compound or composition sufficient to significantly induce a positive modification in the condition to be treated, but low enough to avoid serious side effects.

As used herein, "pharmaceutically-acceptable" means that drugs, medicaments or inert ingredients which the term describes are suitable for use in contact with the tissues of humans and lower animals without undue toxicity, incompatibility, instability, irritation, allergic responses, and the like.

As used herein, "regulating hair growth" means decreasing the rate of hair growth and/or inducing the formation of fewer hair strands, and/or decreasing the diameter of the hair strand, and/or shortening the hair strand and/or preventing, retarding, suppressing or arresting the process of hair growth.

Compositions useful for regulating hair growth preferably comprise from about 0.005% to about 25% DEDCA, more preferably from about 0.1% to about 15%, still more preferably from about 1% to about 10%, most preferably from about 2% to about 7%, also preferably about 5%.

The Carrier

The compositions of the present invention comprise a solid, semi-solid or liquid cosmetically acceptable and/or pharmaceutically-acceptable carrier to enable DEDCA to be delivered to the desired target at an appropriate concentration. The carrier can itself be inert or it can possess physiological or pharmaceutical benefits of its own. DEDCA is topically applied to the skin of a subject in need of treatment. Topical application is preferably achieved with compositions in the forms of lotions, solutions, ointments, sprays, tonics, creams, bars, cream rinses, gels, sticks, mousses, pastes and the like.

Topical compositions of the present invention can be formulated as liquids, for example as a lotion, mousse or milk. Such liquid compositions may be formulated for use in conjunction with an applicator such as a roll-ball applicator, a tined applicator, a pad applicator, or a spray device such as an aerosol can containing propellant, or a container fitted with a pump to dispense the liquid product, or a liquid-impregnated fabric, such as a tissue wipe.

Alternatively, the compositions of the invention can be solid or semi-solid, for example sticks, creams or gels. Such solid or semi-solid compositions may be formulated for use in conjunction with a suitable applicator or simply a tube, jar or other convenient container.

The selection of a carrier for this purpose presents a wide range of possibilities depending on the required product form of the composition. Suitable vehicles can be classified as described hereinafter.

The term "topical carrier" refers to substances which can act as diluents, dispersants, or solvents for DEDCA which therefore ensure that it can be applied to and distributed evenly over the selected target at an appropriate concentration. Topical carriers useful in compositions of the subject invention can include water as a vehicle, and at least one pharmaceutically-acceptable vehicle other than water.

The topical carrier is preferably one which can aid and/or enhance penetration of DEDCA into the skin to reach the immediate environment of the hair follicle. Carriers useful in topical compositions according to the invention may include penetration enhancers such as liposomes, latex lattices, microspheres, cyclodextrans and various forms of microencapsulation of DEDCA. A preferred amount of penetration enhancing agent is from about 1% to about 5% of the composition.

Generally, the carrier is either aqueous or organic in nature or an aqueous emulsion, and is capable of having DEDCA dispersed or dissolved therein. The carder may include pharmaceutically-acceptable and/or cosmetically-acceptable emollients, skin penetration enhancers, coloring agents, fragrances, emulsifiers, thickening agents, and solvents.

Topical compositions of the present invention may be formulated as a composition comprising an emollient. Such compositions typically comprise from about 1% to about 50%, preferably from about 5% to about 20% of a topical pharmaceutically-acceptable emollient; and a safe and effective amount of DEDCA.

As used herein, "emollients" refer to materials used for the prevention or relief of dryness, as well as for the protection of the skin. A wide variety of suitable emollients are known and may be used herein. Such emollients include, but are not limited to, hydrocarbon oils and waxes, silicon oils, triglyceride fats and oils, acetoglyceride esters, ethoxylated glycerides, alkyl esters of fatty acids having 10 to 20 carbon atoms, alkenyl esters of fatty acids having 10 to 20 carbon atoms, fatty acids having 8-22 carbon atoms, fatty alcohols having 8-22 carbon atoms, fatty alcohol ethers, ether-esters, lanolin and derivatives, polyhydric alcohols and their polyether derivatives, wax esters, beeswax derivatives, vegetable waxes, phospholipids, sterols, and amides. SAGARIN, COSMETICS, SCIENCE AND TECHNOLOGY, 2nd Edition, Vol. 1, pp. 32-43 (1972), incorporated herein by reference, contains numerous examples of suitable emollient materials.

Topical compositions of the subject invention may also be formulated as a cream. Preferably the creams of the present invention comprise a safe and effective amount of DEDCA; from about 5% to about 50%, preferably from about 10% to about 25%, of an emollient; and from about 25% to about 95% water. Optionally the cream form contains a suitable emulsifier. When an emulsifier is included, it is in the composition at a level from about 3% to about 50%, preferably from about 5% to about 20%. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pp. 317-324 (1986); the disclosures of which are incorporated herein by reference. Preferred emulsifiers are anionic or nonionic.

Topical compositions of the subject invention may also be formulated as a composition comprising a lotion. Preferably the lotions of the subject invention comprise a safe and effective about of DEDCA; from about 1% to about 50%, preferably from about 3% to about 15% of an emollient; and from about 45% to about 85%, preferably from about 50% to about 75% water. Optionally, the lotion form may contain a suitable emulsifier, comprising from about 3% to about 50%, preferably from about 10% about 20% of the composition. Example of suitable emulsifiers are included hereinabove in the disclosure of cream formulations.

Preferably a solution form of the present invention comprises a safe and effective amount of DEDCA, water and a suitable organic solvent. Suitable organic materials useful as the solvent or a part of a solvent system are as follows: propylene glycol, glycerin, polyethylene glycol (M.W. 200-600), polypropylene glycol (M.W. 425-2025), sorbitol esters, 1,2,6-hexanetriol, ethanol, isopropanol, diethyl tartrate, butanediol, and mixtures thereof.

Gel compositions of the present invention can be formulated by simply mixing a suitable thickening agent to the previously described solution compositions. The gel compositions preferably comprise a safe and effective amount of DEDCA; from about 5% to about 75%, preferably from about 10% to about 50%, of an organic solvent as previously described for solutions; and from about 0.5% to about 20%, preferably from about 1% to about 10% of the thickening agent.

Compositions of solid forms of the present invention have use as stick-type compositions intended for application to the body. Such compositions preferably comprise a safe and effective amount of DEDCA, and from about 50% to about 98%, preferably from about 60% to about 90%, of the previously described emollients. Such compositions can further comprise from about 1% to about 20%, preferably from about 5% to about 15%, of a suitable thickening agent, and optionally emulsifiers and water.

Preferred compositions of the present invention include a safe and effective amount of DEDCA in deodorant compositions, including antiperspirant/deodorant compositions, formulated for topical application to the underarm area. The specific components to be included in the deodorant compositions of the present invention depend upon the particular mode of application desired. These methods of application, as well as the components that may be used in such compositions are well known in the art. Many such compositions are described in S. Plechner, "Antiperspirants and Deodorants", *Cosmetics, Science and Technology*, Vol. 2, pp. 373-416 (M. Balsam and E. Sagarin ed. 1972), incorporated herein by reference.

Preferably, the deodorant compositions of the present invention contain from about 0.01% to about 20%, more preferably from about 0.05% to about 5%, also preferably from about 0.5% to about 2% of an active deodorant agent.

Preferred deodorant agents include non-malodorous disulfides such as bis(pyridine)-2,2'-disulfide, bis(-pyridine)-4,4'-disulfide, bis(2,4-diaminopyridine)-6,6'-disulfide and bis(histidine)-2,2'-disulfide. Preferred deodorant agents also include non-malodorous amines such as para-methylaniline, para-methoxyaniline, para-ethylaniline, para-propylaniline, para-n-butylaniline, para-t-butylanilin, para-methoxyaniline, phenylhydrazine, canaline and aminoacetic acid.

COMBINATION ACTIVES

The compositions of the subject invention may optionally comprise other actives capable of functioning in different ways to enhance the benefits of DEDCA. Examples of such substances include, but are not limited to anti-inflammatories and anti-androgens.

A. Anti-inflammatories

An anti-inflammatory agent may be included as an active in the subject invention, preferably from about 0.1% to about 10%, more preferably from about 0.5% to about 5% of the composition. The exact amount of anti-inflammatory agent to be used in the composition will depend on the particular anti-inflammatory agent utilized since such agents vary widely in potency. Suitable anti-inflammatory agents include steroidal anti-inflammatories, such as hydrocortisone, alpha-methyl dexamethasone, beclomethasone dipropionate, and amcinafel; nonsteroidal anti-inflammatories, such as oxicams, salicylates, acetic acid derivatives, fenamates, pyrazoles and propionic acid derivatives; as well as "natural" anti-inflammatories, such as candelilla wax, alpha bisabolol, aloe vera, Manjistha (extracted from plants in the genus Rubia), and Guggal, (extracted from plants in the genus Commiphora).

B. Anti-androgens

In a preferred composition useful in the subject invention, an anti-androgen is included as an active along with DEDCA. As used herein "anti-androgen" means a compound capable of correcting androgen-related disorders by interfering with the action of androgens at their target organs. The target organ for the subject invention is mammalian skin.

A safe and effective amount of an anti-androgen may be added to the compositions useful in the subject invention, preferably from about 0.001% to about 1%, more preferably from about 0.01% to about 0.1%.

Anti-androgens which are androgen receptor antagonists as well as anti-androgens which are 5-$\alpha$ reductase inhibitors are useful in the compositions of the subject invention. Examples of such anti-androgens are more fully disclosed in U.S. Pat. No. 4,888,336, Holt, Metcalf and Levy, issued Dec. 19, 1989; U.S. Pat. No. 5,110,939, Holt, Metcalf and Levy, issued May 5, 1992; U.S. Pat. No. 5,120,742, Rasmusson and Reynolds, issued Jun. 9, 1992, and U.S. Pat. No. 4,859,681, Rasmusson and Reynolds, issued Aug. 22, 1989; all incorporated herein by reference. See also Stewart, M., and P. Pochi, "Anti-androgens and the Skin", *International Society of Tropical Dermatology*, Vol. 17, No. 3, pp 167-179 (1978); incorporated herein by reference.

Preferred anti-androgens useful in compositions of the subject invention are cyproterone acetate, finasteride, chlormadinone acetate, 17-$\alpha$ propylmesterolone, 17-$\alpha$ estradiol acetate, dienoestrol diacetate, estradiol benzoate, inocoterone acetate, spironolactone and 11-$\alpha$ hydroxyprogesterone.

C. Depilatories

In a preferred composition useful in the subject invention, a depilatory is included as an active along with DEDCA. As used herein, "depilatory" means an agent capable of removing hair from the skin by cleaving the disulfide bonds in hair keratin, thereby causing the hair fiber to disintegrate. A safe and effective amount of depilatory agent may be added to the compositions useful in the subject invention, preferably from about 0.001% to about 1%, more preferably from about 0.05% to about 0.5%.

Preferred depilatories useful in the subject invention include ammonium thioglycate, barium sulfate, calcium thioglycate, ethanolamine thioglycate, mercaptopropionic acid, potassium thioglycate, sodium thioglycate, thioglycerine, thioglycic acid and thioacetic acid.

When depilatories are included in the subject compositions, the pH is preferably from about 7.5 to about 8.5, more preferably about 8.0.

Delivery Methods for Topical Compositions

The topical compositions useful for the methods of the subject invention can be delivered from a variety of delivery devices. The following are two non-limiting examples:

A. Medicated cleansing pads

The compositions useful herein can be incorporated into a medicated pad. Preferably these pads comprise from about 50% to about 75% by weight of one or more layers of nonwoven fabric material and from about 20% to about 50% by weight of a liquid composition deliverable from the nonwoven fabric material preferably comprising from about 0.01% to about 20% DEDCA, more preferably from about 1% to about 10%, more preferably still from about 2% to about 7%, also preferably 5% DEDCA. These pads are described in detail in U.S. Pat. No. 4,891,228, issued to Thaman et al., Jan. 2, 1990; and U.S. Pat. No. 4,891,227, issued to Thaman et al., Jan. 2, 1990; both of which are incorporated by reference.

B. Dispensing devices

The compositions useful herein can also be incorporated into and delivered from a soft-tipped or flexible dispensing device. These devices are useful for the controlled delivery of the compositions to the skin surface and have the advantage that the treatment composition itself never need be directly handled by the user. Non-limiting examples of these devices comprise a fluid container including a mouth, an applicator, means for holding the applicator in the mouth of the container, and a normally closed pressure-responsive valve for permitting the flow of fluid from the container to the applicator upon the application of pressure to the valve.

The valve can include a diaphragm formed from an elastically fluid-impermeable material with a plurality of non-intersecting arcuate slits therein, where each slit has a base which is intersected by at least one other slit, and where each slit is out of intersecting relation with its own base, and wherein there is a means for disposing the valve in the container inside of the applicator. Examples of these applicator devices are described in U.S. Pat. No. 4,693,623, to Schwartzman, issued Sep. 15, 1987; U.S. Pat. No. 4,620,648, to Schwartzman, issued Sep. 15, 1987; U.S. Pat. No. 3,669,323, to Harker et al., issued Jun. 13, 1972; U.S. Pat. No. 3,418,055, to Schwartzman, issued Dec. 24, 1968; and U.S. Pat. No. 3,410,645, to Schwartzman, issued Nov. 12, 1968; all of which are incorporated herein by reference. Examples of applicators useful herein are commercially available from Dab-O-Matic, Mount Vernon, N.Y.

Methods for Regulating Hair Growth

A preferred method of applying the subject compositions involves topical application to the face, underarm, legs and other areas where unwanted hair is likely to grow. The amount of the composition and the frequency of application can vary widely, depending on the area in questions, the desired effect and/or personal needs, but it is suggested as an example that topical application preferably range from about five times daily, to once every other day, more preferably from about three times daily to once daily, and most preferably about twice daily. The composition for topical application will preferably contain from about 0.001 to about 50 mg of DEDCA per $cm^2$ skin receiving the topical composition, more preferably from about 0.01 to about 30 $mg/cm^2$, more preferably still from about 0.05 to about 10 $mg/cm^2$, also preferably from about 0.1 to about 2 $mg/cm^2$. The period of topical application should be as is needed by the individual, and may be over the subject's adult life, for continued regulation of hair growth.

EXAMPLES

The composition embodiments of the present invention are illustrated in the following examples. All pans, percentages, and ratios used herein are by weight unless otherwise specified.

Example I

A topical composition is prepared by combining the following components utilizing conventional mixing techniques.

| Component | % by weight |
| --- | --- |
| DEDCA | 5.0 |
| Propylene glycol | 45.0 |
| Ethanol | 30.0 |
| Water | 20.0 |

1000 mg of the composition per 100 $cm^2$ skin is topically applied to the face twice per day after initial removal of unwanted hair by shaving. Growth of replacement hair is retarded.

Example II

A topical composition is prepared by combining the following components utilizing conventional mixing techniques.

| Component | % by weight |
| --- | --- |
| DEDCA | 2.0 |
| Propylene glycol | 57.0 |
| Ethanol | 20.0 |
| Water | 10.0 |
| Benzyl alcohol | 4.0 |
| Glycerin | 5.0 |
| Myristyl alcohol | 2.0 |

4000 mg of the composition per 100 $cm^2$ skin is topically applied once a day to the legs after initial removal of unwanted hair by shaving. Growth of replacement hair is suppressed.

Example III

A topical composition is prepared by combining the following components utilizing conventional mixing techniques.

| Component | % by weight |
| --- | --- |
| DEDCA | 1.0 |
| Propylene glycol | 30.0 |
| Glycerin | 3.0 |
| Water | 66.0 |

2000 mg of the composition per 100 $cm^2$ skin is topically applied twice per day to the underarm area after initial removal of unwanted hair by waxing. Growth of replacement hair is retarded.

Example IV

A topical composition is prepared by combining the following components utilizing conventional mixing techniques.

| Component | % by weight |
| --- | --- |
| DEDCA | 0.5 |
| Propylene glycol | 30.0 |
| Propylene glycol laurate | 1.0 |
| Isopropanol | 20.0 |
| Water | 48.5 |

500 mg of the composition per 100 $cm^2$ skin is topically applied once per day to the legs after initial removal of unwanted hair by sharing. Growth of replacement hair is retarded.

Example V

A lotion is prepared by combining the following components utilizing conventional mixing techniques.

| Component | % by weight |
| --- | --- |
| DEDCA | 5.0 |
| Di-partially hydrogenated tallow dimethyl ammonium chloride | 4.0 |
| Cetyltrimethyl ammonium chloride | 2.0 |
| DC-200 fluid (12500 csk)* | 1.0 |
| Citric acid | 3.5 |
| Ethylene glycol distearate | 1.5 |
| PEG-3 $C_{12}$ alkyl amide | 3.0 |
| Water | 80.0 |

*Dimethylpolysiloxane available from Dow Chemical Co.

100 mg of the composition per 100 $cm^2$ skin is topically applied to the face three times a day after initial removal of unwanted hair by waxing. Growth of replacement hair is suppressed.

Examples VI-VIII

Lotions are prepared, containing the following compositions, using conventional mixing techniques:

| | Example No. | | |
| --- | --- | --- | --- |
| | VI | VII | VIII |
| Component | % by weight | % by weight | % by weight |
| DEDCA | 0.1 | 0.5 | 2.0 |
| Hydroxylethyl cellulose | 0.4 | — | 0.4 |
| Absolute ethanol | 15.0 | 15.0 | 15.0 |
| Propane-1,2-diol | — | — | 30.6 |
| Butane-1,3-diol | 33.4 | 33.4 | — |

-continued

| Component | Example No. VI % by weight | VII % by weight | VIII % by weight |
|---|---|---|---|
| Paramethyl benzoate | 0.2 | 0.2 | 0.2 |
| Perfume | 0.5 | 0.5 | 0.5 |
| Water | 50.4 | 50.4 | 48.7 |

Use of an amount of any of the above compositions to deposit about: 750 mg per 100 cm² of the composition to the underarm area once a day is appropriate after initial removal by shaving. Growth of replacement hair is retarded.

Example IX

A water-in-oil emulsion is prepared by combining the following ingredients, using conventional mixing techniques:

| Component | % by weight |
|---|---|
| Oily Phase | |
| DEDCA | 5.0 |
| Cetearyl alcohol | 5.0 |
| Silicon oil, 200 fluid | 1.0 |
| Isopropyl myristate | 2.0 |
| Sodium stearoyl-2-lactylate | 2.0 |
| Aqueous Phase | |
| Propylene glycol | 5.0 |
| Sodium citrate | 0.2 |
| Perfume | 0.1 |
| Water | 79.7 |

The emulsion is prepared by taking 10 parts of the oily phase and adding it slowly with stirring to 90 parts by volume of the aqueous phase. Use of an amount of the emulsion to deposit about 1000 mg per 100 cm² of the emulsion three times a day to the legs is appropriate, after initial hair is removed by shaving. Growth of replacement hair is retarded.

Example X

An oil-in-water cream is prepared by mixing the following components:

| Component | % by weight |
|---|---|
| Oily Phase | |
| DEDCA | 5.0 |
| Sorbitan monoleate | 20.0 |
| Quaternium-18-hectonite | 5.0 |
| Liquid paraffin | 60.0 |
| Aqueous Phase | |
| Xanthan gum | 1.0 |
| Preservative | 0.3 |
| Perfume | 0.2 |
| Water | 8.5 |

The cream is prepared by mixing the oily phase and heating to 65° C. The aqueous phase is combined and heated to 70° C. The aqueous phase is added to the oil phase with suitable agitation. Moderate agitation is applied while cooling. About 5 mg of the cream is deposited per 100 cm² on the face once a day after removal of initial hair by waxing. Growth of replacement hair is suppressed.

Example XI

A deodorant composition is prepared, containing the following components, using conventional mixing techniques:

| Component | % by weight |
|---|---|
| DEDCA | 1.0 |
| Ethyl Acetate | 29.7 |
| Cyclodecamethylpentasiloxane | 68.0 |
| 5-chloro-2-(2,4-dichlorophenoxy)-phenol | 0.3 |
| Para-methylaniline | 1.0 |

3500 mg of the deodorant composition per 100 cm² skin is topically applied to the underarm area after initial removal of the unwanted hair by shaving. Growth of replacement hair is retarded.

Example XII

A deodorant composition is prepared, containing the following components, using conventional mixing techniques:

| Component | % by weight |
|---|---|
| DEDCA | 4.0 |
| Acetone | 26.7 |
| Cyclodecamethylpentasiloxane | 68.0 |
| 5-chloro-2-(2,4-dichlorophenoxy)-phenol | 0.3 |
| Bis(pyridine)-2,2'disulfide | 1.0 |

2000 mg of the deodorant composition per 100 cm² skin is topically applied to the underarm area after initial removal of unwanted hair by shaving. Growth of replacement hair is suppressed.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

What is claimed is:

1. A method of regulating hair growth in mammals comprising topically applying to a mammal in need of treatment a composition comprising:
    a) a safe and effective amount of diethyldithiocarbamic acid ("DEDCA") having the structure:

$HSC(S)-N-(C_2H_5)_2$ 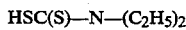

or a pharmaceutically-acceptable salt thereof; and
    b) a safe and effective amount of a topical carrier.

2. The method of claim 1 wherein the amount of DEDCA applied to the skin is from about 0.001 mg per cm² skin to about 50 mg per cm² skin.

3. The method of claim 2 wherein the amount of DEDCA applied to the skin is from about 0.01 mg per cm² skin to about 30 mg per cm² skin.

4. The method of claim 3 wherein the amount of DEDCA applied to the skin is from about 0.05 mg per cm² skin to about 10 mg per cm² skin.

5. The method of claim 4 wherein the amount of DEDCA applied to the skin is from about 0.1 mg per cm² skin to about 2 mg per cm² skin.

6. A method of regulating growth of replacement hair comprising the steps of:
   a) removing unwanted hair from a given region on the skin of a mammal in need of treatment; and
   b) topically applying to the region a safe and effective amount of a composition comprising;
      i) a safe and effective amount of DEDCA; and
      ii) a safe and effective topical carrier.

7. The method of claim 6 wherein the amount of DEDCA applied to the skin is from about 0.001 mg per $cm^2$ skin to about 50 mg per $cm^2$ skin.

8. The method of claim 7 wherein the amount of DEDCA applied to the skin is from about 0.01 mg per $cm^2$ skin to about 30 mg per $cm^2$ skin.

* * * * *